(12) United States Patent
Hayek

(10) Patent No.: US 6,310,090 B1
(45) Date of Patent: Oct. 30, 2001

(54) PROCESS AND PRODUCT FOR ENHANCING IMMUNE RESPONSE IN COMPANION ANIMALS USING A COMBINATION OF ANTIOXIDANTS

(75) Inventor: Michael G. Hayek, Dayton, OH (US)

(73) Assignee: The Iams Company, Dayton, OH (US)

( * ) Notice: Subject to any disclaimer, the term of this patent is extended or adjusted under 35 U.S.C. 154(b) by 0 days.

(21) Appl. No.: 09/579,694

(22) Filed: May 26, 2000

Related U.S. Application Data (60) Provisional application No. 60/136,176, filed on May 27, 1999.

(51) Int. Cl.[7] .......................... A61K 31/355; A61K 31/07
(52) U.S. Cl. ............................................. 514/458; 514/725
(58) Field of Search ...................................... 514/725, 458

(56) References Cited

U.S. PATENT DOCUMENTS

| | | |
|---|---|---|
| 5,290,605 | 3/1994 | Shapira . |
| 5,567,424 | 10/1996 | Hastings . |
| 5,596,011 | 1/1997 | Repine et al. . |
| 5,643,623 | 7/1997 | Schmitz et al. . |
| 5,733,884 | 3/1998 | Barbul et al. . |
| 5,770,217 | 6/1998 | Kutilek, III et al. . |
| 5,834,044 | 11/1998 | Schmitz et al. . |

FOREIGN PATENT DOCUMENTS

| | | |
|---|---|---|
| 0 845 216 A1 | 6/1998 | (EP) . |
| WO 98 44808 | 10/1998 | (WO) . |

OTHER PUBLICATIONS

Haq et al., Effect of beta–Carotene, Canthaxanthin, Lutein, and Vitamin E on Neonatal Immunity of Chicks When Supplemented in the Broiler Breeder Diets, Poultry Science 75, 1996, pp. 1092–1097.

Meydani et al., Vitamin E and Immune Response in Aged Dogs, Iams Nutrition Sumposium Proceedings, 1998, pp. 295–303, vol. II.

Primary Examiner—Raymond Henley, III
(74) Attorney, Agent, or Firm—Killworth, Gottman, Hagan & Schaeff, L.L.P.

(57) ABSTRACT

A process for feeding a companion animal such as a dog a diet containing an effective amount of a combination of antioxidants to enhance immune response and improve the overall health of the animal is provided. Preferably, the diet includes from about 175 to about 400 IU of vitamin E per kilogram of diet, from about 1 to about 50 mg/day of lutein, and from about 1 to about 50 mg/day of β-carotene.

8 Claims, 2 Drawing Sheets

PROCESS AND PRODUCT FOR ENHANCING IMMUNE RESPONSE IN COMPANION ANIMALS USING A COMBINATION OF ANTIOXIDANTS

CROSS REFERENCE TO RELATED APPLICATIONS

This application claims the benefit of U.S. provisional application Serial No. 60/136,176, filed May 27, 1999.

BACKGROUND OF THE INVENTION

This invention relates to a process and product for enhancing immune response and improving the overall health of companion animals such as dogs, and more particularly, to a process and product which provides beneficial amounts of antioxidants in the animal's diet.

In recent years, there has been increasing interest in the health benefits of antioxidants. Antioxidants are nutrients that counteract the effect of reactive oxygen species (also known as free radicals). These harmful molecules are by-products of normal metabolism. Antioxidant nutrients counteract the effects of free radicals by attaching to these molecules, neutralizing them, and removing them from the body. Inefficient clean-up of free radicals has been implicated in causing damage to humans, which is believed to result in certain diseases such as Alzheimer's disease, autoimmune disease, cancer, cardiovascular disease, cataracts, diabetes, macular degeneration, multiple sclerosis, muscular dystrophy, pancreatitis, Parkinson's disease, and rheumatoid arthrititis. The damage caused by the accumulation of these free radicals may be responsible for the aging process as the accumulation of these free radicals over time causes the suppression of the immune response that occurs with age, resulting in increased incidence of disease within the senior population.

Antioxidant nutrients are a classification for a variety of compounds with a similar role of neutralizing harmful free radicals. They can include such commonly known vitamins as vitamin A, vitamin C, and vitamin E. They also include other compounds that are classified as carotenoids. Examples of carotenoids include β-carotene, lutein, astaxanthin, canthoxanthin and lycopene. These compounds are responsible for developing the green, yellow, orange and pink pigmentation found in fruits, flowers and vegetables. These carotenoids are known to play an important role in modulating the immune system (for example, canthaxanthin has been found to prevent chemical-induced carcinogenesis in mice as well as increase lymphocyte proliferation in rats). Astaxanthin and β-carotene have been found to increase ex vivo antibody response of mouse splenocytes to T-dependent antigens. Dietary lutein has been found to enhance lymphocyte proliferation in mouse splenocytes.

Although these compounds are all classified as antioxidants, it has become apparent that they do not all function in the same way. For instance, historical studies in humans show that populations consuming diets high in antioxidants (i.e., high intake of fruits and vegetables) have a lower incidence of cancer than other groups of people. However, clinical studies that provide supplementation with antioxidants such as vitamin E or β-carotene alone do not provide the same magnitude of protection. It is currently believed that a human health benefit from antioxidant nutrients may be through a combination of several different antioxidants at low levels rather than one antioxidant at high levels.

Although the dog has not evolved on a diet based on high quantities of fruits and vegetables, it did hunt and eat small herbivores that consumed plants having high concentrations of these compounds. Therefore, it is possible that the dog's need for antioxidants evolved naturally. Accordingly, there is a need in the art for providing beneficial antioxidants in the diet of a companion animal such as a dog to provide health benefits.

SUMMARY OF THE INVENTION

The present invention provides a process for feeding a companion animal such as a dog a diet containing an effective amount of a combination of antioxidants to enhance immune response and improve the overall health of the animal. Preferably, the animal is fed a diet which includes a combination of vitamin E, lutein, and β-carotene. This antioxidant package provides the animal with from about 175 to about 400 IU of vitamin E per kilogram of diet, about 1 to about 50 mg/day of lutein, and from about 1 to about 50 mg/day of β-carotene. Such a diet has been found to optimize immune cells in dogs as well as increase vaccine recognition in dogs.

Accordingly, it is a feature of the present invention to provide a pet food and process for enhancing immune response and improving the overall health of companion animals such as dogs by providing an effective amount of a combination of antioxidants in the diet of the animal. This, and other features and advantages of the present invention, will become apparent from the following detailed description, the accompanying drawings, and the appended claims.

DETAILED DESCRIPTION OF THE PREFERRED EMBODIMENTS

The present invention provides a process for feeding a companion animal such as a dog a diet containing a combination of antioxidants to enhance immune response and improve the overall health of the animal. The combination of antioxidants may be provided to the animal either as a supplement or contained in a diet fed to the animal. Such a supplement may be in the form of a pill or capsule, a treat or a biscuit, or any other edible form. By "diet", it is meant the food or drink regularly consumed by the animal. By using a combination of antioxidants, it is believed that health benefits are provided to many areas of the immune system, e.g., optimized immune cell activation, increased antibody levels, and improved vaccine recognition.

The diet can be any suitable pet food formula which also provides adequate nutrition for the animal. For example, a typical canine diet for use in the present invention may contain about 18–40% crude protein, about 4–30% fat, and about 4–20% total dietary fiber. However, no specific ratios or percentages of these or other nutrients are required. The combination of antioxidants may be blended with such diet to provide the beneficial amounts needed.

In order that the invention may be more readily understood, reference is made to the following examples which are intended to illustrate the invention, but not limit the scope thereof.

EXAMPLE 1

Vitamin E

Twenty young (mean age 2 years) and 20 old (mean age 9.2 years) Beagles were fed a standard commercial chicken/corn-based diet formulated to contain 27 IU/kg diet of vitamin E (NRC recommendation) (control diet) for 1 month prior to the commencement of the experiment in order to stabilize the dogs' vitamin E levels. Young and old dogs were then randomly assigned to the diets containing 27 IU/kg diet of vitamin E or 280 IU/kg diet of vitamin E for 8 weeks. Blood was collected before and after 8 weeks of dietary treatments for measurement of plasma vitamin E levels and assessment of lymphocyte mitogenic response to ConA (concanavalin A) and PHA (phytohemagglutinin). Prior to dietary treatment and similar to other species, old dogs had significantly lower mitogenic response to PHA and ConA than young dogs. Surprisingly, there was a significant decrease in plasma vitamin E level of young and old dogs fed 27 IU/kg diet of vitamin E with the young dogs exhibiting a higher percentage decrease (35% in old v. 50% in young, P=0.12). Examination of the vitamin E content of the commercial chow fed to the study dogs before their arrival at the facility indicated that on average, the commercial chow contained 60 IU/kg diet of vitamin E. Thus, decline in plasma vitamin E levels can be attributed to the lower levels of vitamin E in the control diet compared to that of commercial dog chow. Both young and old dogs supplemented with vitamin E showed a significant increase in plasma vitamin E levels, with the young dogs exhibiting a significantly higher percent increase than old dogs (20% in old v. 50% increase in young dogs, P=0.02). The young dogs fed the 27 IU/kg diet of vitamin E also had a significant decrease in ConA and PHA-stimulated proliferation during the 8 week feeding period. No such decrease was observed in dogs supplemented with 280 IU/kg diet of vitamin E. The old dogs fed 27 or 280 IU/kg diet of vitamin E did not show a significant change in mitogen-stimulated lymphocyte proliferation.

β-carotene

Female Beagle dogs (18 to 19 months of age; 7 to 9 kg body weight) were fed a basal diet (The Iams Co., Lewisburg, OH) which met or exceeded the requirement for all essential nutrients. Animals were housed indoors in light- (14 hr light; 10 hr dark) and temperature-controlled rooms. A test was conducted to study the uptake profile of β-carotene after a single oral dose of β-carotene.

To study the uptake of oral β-carotene in dogs given a single dose of β-carotene orally, dogs (n=6/treatment) were given once perorally 0, 50, 100 or 200 mg of β-carotene (10% cold water dissolvable; BASF Corp., Ludwigshafen, Germany). The appropriate dose of β-carotene was dissolved in 5 ml of water fed orally by using a feeding syringe. In order to establish appropriate sampling times, two dogs were used in a preliminary study. These dogs were fed once with 50 mg β-carotene and blood sampled at 0 (immediately prior to β-carotene feeding), 3, 6, 9, 12, 15, 18, 21 and 24 hr.

Blood plasma was separated by centrifugation and β-carotene concentrations were analyzed using high performance liquid chromatography (HPLC) as follows. All procedures were conducted under dim light. Duplicate aliquots of plasma, each leukocyte homogenate, and each leukocyte subcellular fraction were extracted with a 1:1 mixture of diethyl ether and petroleum ether in the presence of BHT. The ether phase was removed and dried under a stream of nitrogen. The residue was reconstituted in mobile phase for the HPLC determination of β-carotene. Samples (50 µl) were injected onto a 5 µm spherical C-18 reverse-phase column (3.9×150 mm; Resolve) and eluted with a 47:47:6 (v/v/v) mixture of acetonitrile, methanol, and chloroform at a flow rate of 1.0 ml/min.

Results from this example showed peak concentrations of β-carotene occurring between 3 and 6 hr post-dosing and were undetectable by 24 hr. Subsequently, blood was sampled from the remaining dogs at the same time periods. Plasma was similarly separated and analyzed by HPLC.

Concentrations of plasma β-carotene was undetectable in unsupplemented dogs at all time periods studied. In contrast, there was a dose-dependent increase (P<0.01) in plasma β-carotene in dogs given an oral dose of β-carotene. Peak concentrations were observed at 6 hr post-dosing and were consistent in all treatment groups. Thereafter, there was a rapid decrease (P<0.01) in β-carotene concentrations in all β-carotene supplemented dogs. Concentrations were undetectable by 24 hr post-dosing. The half-life of plasma β-carotene was approximately 3 (50 and 100 mg doses) to 4 (100 mg dose) hours. Peak concentrations of blood β-carotene occurred earlier in dogs than in cats (see Examples 4 and 5 below). Also, concentration of β-carotene in the plasma of dogs are approximately 10 to 16 fold lower than that observed in cats after adjusting for differences in body weight.

In a second study, the dogs (n=6/treatment) were fed daily at 0800 hr for 7 consecutive days with 0, 12.5, 25, 50 or 100 mg β-carotene. The β-carotene was top-dressed on the food and fed in the morning meal. Blood was sampled once daily on day 0 (immediately prior to the first dose) and subsequently at 6 hr after each dosing (days 1 through 7). This blood sampling time was chosen based on the results obtained in Example 1 which showed peak concentrations of β-carotene at 6 hr after a dose. Plasma was isolated and analyzed for concentrations of β-carotene.

Daily dosing of dogs with β-carotene for 7 days produced a dose-dependent increase (P<0.01) in circulating β-carotene. Dogs fed 100 mg of β-carotene showed the steepest increase in daily concentrations of plasma β-carotene. Peak concentrations (18 µg/L) of plasma β-carotene on day 1 in dogs fed 100 mg β-carotene in this example was similar to that observed in the first study. Concentrations of plasma β-carotene after the last dose was generally 2.5 to 4 fold higher than that observed after the first dose.

A third study was designed to study the uptake of β-carotene in dogs by blood lymphocytes. The dogs (n=8/treatment) were fed 0, 50 or 100 mg of β-carotene daily for 30 days. Blood was sampled from all dogs via the jugular vein on days 10, 20 and 30. Blood lymphocytes and neutrophils were separated by density gradient centrifugation. Cell numbers were enumerated. Lymphocytes and neutrophils were resuspended in PBS containing 3% sodium ascorbate as an antioxidant. An aliquot of the cell suspension was sonicated for 30 seconds to disrupt the cells. The leukocyte homogenates were extracted for HPLC analysis of β-carotene.

On day 30, a larger aliquot of blood was taken and leukocyte suspensions prepared as described above for subsequent subcellular fractionation. Cells were disrupted by sonication for 20 seconds in 5 volumes of 0.25 M sucrose. Sodium ascorbate was added as the antioxidant. The homogenate was centrifuged (600×g for 10 min at 4° C.) and the nuclear pellet separated from the supernatant. The postnuclear supernatant was centrifuged (17,300×g for 20 min at 4° C.) to separate the mitochondrial fraction. The postmitochondrial supernatant was centrifuged (102,000×g for 60 min at 4° C.) to separate the microsomal from the cytosolic fraction. Each subcellular fraction was analyzed for β-carotene content by HPLC.

On day 0 (prior to β-carotene supplementation), concentrations of β-carotene in peripheral blood lymphocytes were undetectable in all dogs. Also, β-carotene in lymphocytes from unsupplemented dogs remained undetectable throughout the study. In contrast, β-carotene concentrations in lymphocytes from dogs fed β-carotene generally increased ($P<0.01$) in a time-dependent manner. There was no significant treatment difference in β-carotene concentrations in lymphocytes when comparing dogs fed 50 versus 100 mg β-carotene.

β-carotene was not detectable in the various subcellular fractions of lymphocytes obtained from unsupplemented dogs. In contrast, β-carotene was taken up by all subcellular fractions of blood lymphocytes isolated from β-carotene-supplemented dogs. The cytosol fraction accounted for 52 to 62% of the total β-carotene in the lymphocytes while the nuclei contained the lowest (6 to 8%) amount of total β-carotene. The mitochondria (14 to 17%) and microsomes (16 to 23%) were intermediate between the cytosol and the nuclei. The dose of dietary β-carotene did not have a significant influence on β-carotene uptake by the subcellular fractions on day 30 of feeding. The results show that β-carotene was taken up by all lymphocyte subcellular fractions. However, β-carotene was highest in the cytosol.

As with lymphocytes, blood neutrophils similarly take up β-carotene. However, unlike lymphocytes, maximal uptake occurred by day 10, with no further increase in neutrophil β-carotene concentrations observed on day 30. The cytosol, mitochondria and microsomes of blood neutrophils also showed significant uptake of β-carotene. In contrast, β-carotene was not detected in the nuclei. As with blood lymphocyte subcellular fractions, β-carotene was the highest (61 to 68) in the cytosolic fraction of blood neutrophils. No significant dose effect was observed.

In a fourth study, female Beagles (4 to 5 mo old) were supplemented daily with 0, 25, 50 or 100 mg of β-carotene to study the role of dietary β-carotene in enhancing the cell-mediated and humoral immune systems of the dog. The following parameters were assessed in all the animals or in the peripheral blood lymphocytes: (1) delayed-type hypersensitivity (DTH) against PHA (nonspecific immunity) and vaccine (specific immunity), (2) lymphocyte proliferation, (3) lymphocyte populations and (4) immunoglobulins (Ig).

β-carotene supplementation increased plasma β-carotene concentrations in a dose-dependent manner but did not influence plasma retinol or α-tocopherol. These changes generally reflected the DTH response to both the specific (vaccine) and non-specific (PHA) antigens. The greatest response to PHA challenge was observed in dogs fed 50 mg of β-carotene whereas dogs fed either 20 or 50 mg of β-carotene showed significantly higher DTH response to the vaccine. Delayed type hypersensitivity is strictly a cellular reaction involving T cells and macrophages without involving an antibody component. Antigen presenting cells (e.g., macrophages) present the antigen or allergen to T cells that become activated and release lymphokines. These lymphokines activate macrophages and cause them to become voracious killers of the foreign invaders. Therefore, the data show a heightened cell-mediated response in dogs fed β-carotene.

β-carotene feeding also produced significant changes in lymphocyte subsets. Compared to controls, dogs fed 20 or 50 mg of β-carotene had an elevated population of CD4+ cells (week 8). Dogs fed 20 mg of β-carotene also had elevated population of CD8 cells in weeks 2 and 4. The T cells can be classified according to the expression of CD4 membrane molecules. The CD4 functions as an adhesion molecule and as a co-signaling co-receptor. It plays a role in T cell activation. The CD4+ T lymphocytes recognize antigen in association with the class II MHC molecules and largely function as helper cells. The increase in T helper cell population in this study can explain the corresponding increase in DTH response in dogs fed 20 to 50 mg of β-carotene.

Concentrations of IgG, IgM and total IgG increased significantly in dogs fed β-carotene as early as 1 week after dietary supplementation. Increases in Ig were dose dependent for dogs fed 0 to 20 mg of β-carotene. The highest level of β-carotene (50 mg) did not produce a further increase. Dogs fed 20 mg of β-carotene consistently had the greatest antibody response for both Ig. One of the major functions of the immune system is the production of antibodies which circulates freely to protect the body against foreign materials. Antibodies serve to neutralize toxins, immobilize certain microorganisms, neutralize viral activity, agglutinate microorganisms or antigen particles and precipitate soluble antigens.

β-carotene feeding did not influence mitogen-induced lymphocyte blastogenesis and IL-2 production. Lymphocytes are involved in cell-mediated immunity. Upon recognizing an antigen, lymphocytes will divide rapidly, thereby cloning themselves in preparation for combating a potential invasion. In humoral immune response, IL-2 stimulates both T helper cells and B cells to proliferate in response to antigens. It is required for the clonal expansion of antigen- or mitogen-activated T cells. In cell-mediated immune response, IL-2 activates natural killer cells, stimulates thymocyte proliferation and induces cytotoxic T cell activity Based on the results of these experiments, the dog absorbs a significant amount of β-carotene from the diet and transfers the β-carotene into the subcellular organelles of immune cells and phagocytes. In these cells, β-carotene appears to enhance the immune system of the dog through enhanced cell-mediated immune responses (DTH response, shift in lymphocyte subsets) and humoral response (IgG and IgM production).

Lutein

Fifty six female Beagle dogs (17 to 18 months old; average body weight 11.4±0.4 kg) were randomly assigned to be supplemented daily with 0, 5, 10 or 20 mg lutein for 17 weeks. The lutein contained 76.66% lutein and 5.23% zeaxanthin. The lutein supplement was resuspended in soybean oil to the appropriate concentration and 1 mL administered perorally at 0800 h daily. Food (200 g/dog/d) was offered immediately after the lutein supplementation. The basal diet met or exceeded the requirements for all essential nutrients (NRC 1985). All dogs were housed in 2×2 m pens (2 dogs/pen) in a temperature (20 to 22° C.) and light (14 h light) controlled facility. Body weight was recorded at weeks 0, 6, and 12.

Blood was collected by jugular venipuncture into heparinized evacuated tubes on weeks 0, 2, 4, 8 and 12 and aliquots used for HPLC analysis and for assessing immune responses.

Extraction and HPLC Analysis

Plasma was extracted for analysis of lutein, zeaxanthin, retinol and α-tocopherol. Briefly, plasma protein was precipitated by adding an equal volume of ethanol containing 0.1 % butylated hydroxytoluene (BHT) (Aldrich Chemical Co., Milwaukee, Wis.). The mixture was extracted with 5 mL of a 1:1 mixture of petroleum ether:anhydrous diethyl ether.

The dried residue was resuspended in mobile phase consisting of a 47:47:6 (v:v:v) mixture of HPLC-grade acetonitrile: methanol: chloroform (Fisher Scientific, Fair Lawn, N.J.). Lutein, zeaxanthin and α-tocopherol were quantitated by comparing the area under the curve whereas retinol was quantitated using peak height. The identity of the eluted compounds was confirmed by comparing their absorption spectrum with that of pure standards. Because baseline separation of lutein and zeaxanthin was not accomplished, plasma concentrations were reported as lutein+zeaxanthin.

Delayed Type Hypersensitivity Response

Skin induration response was assessed in all dogs on weeks 0, 6, and 12. Dogs were injected intradermally in the flank area with saline (8.5 g/L; control), an attenuated polyvalent vaccine containing canine distemper virus, canine adenovirus type-2, canine parainfluenza virus and parvovirus (Vanguard 5, Smithkline Beacham, West Chester, Pa.; specific antigen), and PHA (0.5 g/L; nonspecific antigen). The doses of vaccine and PHA used were previously determined to provide optimal skin response in Beagle dogs of similar age. The injection site was clipped and wiped with 70% ethyl alcohol. The injection volume was 100 μL. Skin induration was measured at 0, 24, 48 and 72 h post-injection with the aid of a pressure-sensitive digital micrometer (Mitsutoyo, Tokyo, Japan) and response was expressed as a percentage of skin thickness measured at 0 h.

Lymphocyte Proliferation

Blood collected on weeks 0, 2, 4, 8 and 12 were used to assess mitogen-induced lymphocyte proliferation by peripheral blood mononuclear cells (PBMC). Whole blood culture was used in order to mimic in vivo conditions. Mitogens used were phytohemagglutinin (PHA), concanavalin A (Con A) and pokeweed mitogen (PWM). Whole blood was thoroughly mixed and then diluted 1:12 with RPMI-1640 containing 25 mM of Hepes, penicillin (100 U/mL) and streptomycin (100 μg/mL) (Sigma, St. Louis, Mo.). Preliminary studies using undiluted blood and blood diluted 1:2, 1:4, 1:8, 1:12 and 1:16 showed optimal PBMC proliferative response with a 1:12 dilution. Triplicate 150 μL volumes were pipetted into 96-well round bottom plates and 50 μl of the appropriate mitogens added. The final concentrations of the mitogens in culture were 2 and 10 μg/mL for PHA, 1 and 5 μg/mL for Con A and 0.5 and 2.5 μg/mL for PWM. The two mitogen concentrations gave maximum (the higher mitogen concentration) and suboptimal (lower mitogen concentration) proliferative responses in preliminary studies using blood from similar animals. The mixture was incubated for 72 h at 37° C. in a humidified incubator under a 5% $CO_2$ atmosphere. Four hours prior to the termination of the incubation period, 20 μL of [$^3$H]-thymidine (1 [μCi/well) were added. Cells were harvested onto fiberglass filters and radioactivity was counted by liquid scintillation. Proliferation response of PBMC was expressed as stimulation index (cpm of stimulated cultures/cpm of unstimulated cultures).

Lymphocyte Subsets

Blood leukocytes were separated using Histopaque-1119 (Sigma, St. Louis, Mo.). Cells were washed three times with phosphate-buffered saline (PBS, pH 7.4) and contaminating erythrocytes were lysed in $NH_4Cl$ (8.4 g/L). Lymphocyte subsets were determined by flow cytometry (FACScan, Becton Dickinson, San Jose, Calif.). Isolated mononuclear cells were resuspended to $1 \times 10^7$ cells/mL in PBS supplemented with 2% gamma globulin-free serum, 5% goat serum and 0.2 g/L sodium azide. For immunofluorescence analysis, a total of $5 \times 10^5$ cells were incubated for 30 minutes on ice with optimal concentrations of mouse anti-canine monoclonal antibody (mAb). The mAb used were specific for the following lymphocyte subsets: total T cells (anti-CD5), T-helper cells (anti-CD4), T-cytotoxic/suppressor cells (anti-CD8), lymphocytes expressing major histocompatability complex (MHQ class II antigens (anti-MHC class II), and B cells (anti-CD21). Cells were then washed three times and incubated with a secondary antibody, fluorescein isothiocyanate (FITC)-conjugated goat F(ab')$_2$ anti-mouse IgG+IgM (H+L) (Caltag, Burlingame, Calif.), for 30 minutes on ice to visualize the bound mAb. Stained cells were fixed in 4% paraformaldehyde in preparation for acquisition.

Appropriate negative controls were included to correct for background fluorescence. Data were expressed as the percentage of positive-staining cells corrected for cells stained nonspecifically with the secondary antibody.

NK Cell Cytotoxicity

Canine thyroid adenocarcinoma cells were used as target cells in assessing NK cell cytotoxic activity. This cell line was previously shown to be susceptible to killing by canine NK cell. Target cells were cultured in a T75 flask with 20 mL minimum essential medium (MEM; Sigma Chem. Co., St. Louis, Mo.) supplemented with 10% fetal calf serum (FCS), 100 U/mL of penicillin and 100 μg/mL of streptomycin. When confluent, target cells were trypsinized, washed 3 times and resuspended to $5 \times 10^5$ cells/mL in complete medium (RPMI-1640+10% FCS+100 U/mL of penicillin+ 100 μg/mL of streptomycin). Triplicate 100 μL aliquots of the target cells were pipetted into 96-well U-bottom plates (Costar, Cambridge, Mass.) and incubated for 8 hours to allow cell adherence. Lymphocytes (effector cells; 100 μL) isolated by percoll separation (as described above) were then added to the target cells to provide an effector:target cell (E:T) ratio of 10:1. After 10 hours of incubation at 37° C., 20 μl of a substrate containing 5 μg of 3-(4,5-dimethylthiazol-2-yl)-2,5-diphenyltetrazolium bromide (MTT) was added. The mixture was incubated for 4 hours at 370° C. after which the unmetabolized MTT was removed by aspiration. The formazan crystals were dissolved by adding 200 μL of 95% ethanol. Optical density was measured at 570 nm using a microplate reader. The percentage of NK cell-specific lysis was calculated as follows:

Specific cytotoxicity (%)=100×{1−[(OD of target cells and effector cells− OD of effector cells)/(OD of target cells)]}

IL-2 Production

Whole blood was diluted 1:2 with RPMI-1640 supplemented with Hepes and antibiotics (described earlier) and 400 μL of diluted blood were pipetted into 48-well plates (Costar, Cambridge, Mass.). Cells were stimulated with PHA (400 μL of a 5 μg/mL solution) for 48 hours at 370° C. in a 5% $CO_2$ atmosphere. The plates were centrifuged at 200×g for 10 minutes and the supernatant was frozen at −80° C. The IL-2 content of the culture supernatant was determined in triplicate by ELISA (Intergen, Purchase, N.Y.). The polyclonal anti-human IL-2 cross-reacted with canine IL-2 and recombinant human IL-2 was used as the standard.

Serum IgG and IgM

Serum collected on weeks 0, 2, 4, 8 and 12 were analyzed for IgG and IgM concentrations by single radial immunodiffusion (SRID). In addition, all dogs were vaccinated with the polyvalent vaccine (Vanguard 5, Smithkline Beacham, West Chester, Pa.) on week 13 and again on week 15 to study the possible anamnestic effect of dietary lutein. Blood was collected weekly from week 13 through week 17. Goat antiserum to canine IgG (10%, whole molecule) or IgM (7.5%, μ chain specific) (ICN, Aurora, Ohio) was mixed with melted agarose (10 g/L in PBS; Sigma Chem. Co., St. Louis, Mo.) and the mixture solidified in SRID plates. Duplicate 5 μL volumes of serum or IgG (0, 2.88, 5.75, 11.5 and 23.0 mg/ml) or IgM (0, 0.25, 0.5, 1.0 and 2.0 mg/ml) standard were loaded into the wells. After incubating for 24 hours at room temperature in a humidified chamber, ring diameters were measured using a SRID reader (Transidyne General Corp., Ann Arbor, Minn.).

Lipid Peroxidation (TBARS) Assay

Plasma lipid peroxidation activity was determined by measuring malondialdehyde (MDA) production. The standard used was 1,1,3,3-tetramethoxypropane JMP) (Sigma Chem. Co., St. Louis, Mo.). Duplicate 500 μL plasma samples were pipetted into 15 ml, glass tubes and 3 mL of 10 g/L phosphoric acid and 1 ml of 6 g/L TBA solution were added. The mixture was boiled in a water bath for 45 minutes. Tubes were allowed to cool and the TBA-MDA complex was extracted with 4 ml of n-butanol. The butanol layer was separated by centrifugation at 1,000×g for 10 minutes and absorbance was measured on at 532 nm (Beckman, Fullerton, Calif.). The TBARS activity was expressed in nmole MDA/L plasma.

Statistics

Data were analyzed by split-plot ANOVA using the General Linear Model of SAS. The statistical model was $Y_{ijk}= \mu Diet_i+Dog_j(Diet)$ (error term used to test the effects of $Diet)+Period_k+Diet_i*Period_k+e_{ijk}$. Differences among treatment means were compared using orthogonal contrast and were considered statistically significant when $P<0.05$.

Results

Plasma

Figure 1:
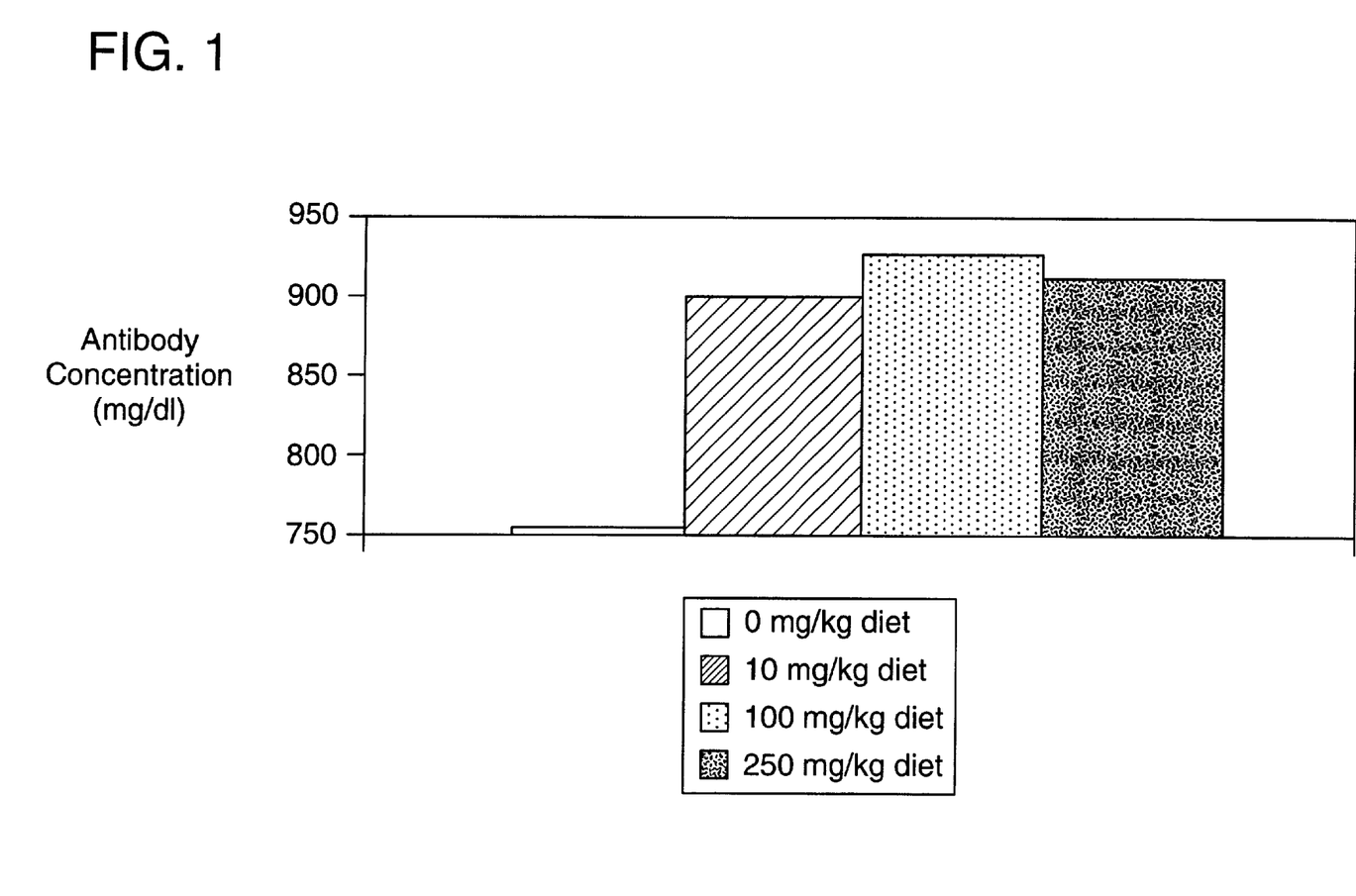
FIG. 1 is a graph of antibody concentration in dogs (mg/dl) versus mg/kg diet of beta-carotene.

Plasma concentrations of lutein+zeaxanthin in lutein-supplemented dogs increased rapidly after 2 weeks of feeding (FIG. 1). Plasma concentrations continued to increase thereafter, although more gradually, in dogs fed 10 and 20 mg lutein. In contrast, plasma lutein+zeaxanthin was not detectable in unsupplemented dogs. Concentrations of plasma lutein+zeaxanthin on weeks 2 through 12 was significantly higher (P <0.05) in dogs fed lutein than in unsupplemented animals. Lutein supplementation did not influence concentrations of plasma retinol and a-tocopherol. Concentrations of these vitamins across all treatments and all periods averaged 3.63±0.14 and 37±2 μmol/L, respectively.

Delayed-type Hypersensitiyity Response

During all periods studied, DTH response to saline was low (3 to 10% increase in skin thickness) and did not differ significantly among treatment groups. Prior to jutein feeding (week 0), DTH responses to PHA and vaccine were similar across all dietary groups. Irrespective of treatment period, maximal DTH response to PHA was observed around 24 h post-injection whereas maximal response to vaccine occurred between 48 and 72 h. Also, skin thickness response to PHA was approximately two times higher than to vaccine.

On week 6, there was a dose-related DTH response to PHA at 24 h post-injection. The DTH response decreased by 48 and 72 h and no significant treatment difference was observed during these times. The DTH response to vaccine was dose-related at 48 and 72 h post-injection and was not significant at 24 h.

On week 12, there was a general dose-dependent increase in DTH response to PHA at 24, 48 and 72 h; however, the response was significantly higher for dogs fed 20 mg lutein compared to unsupplemented dogs. In contrast to week 6, there was no significant dietary effect on DTH response to vaccine.

Mitogen-induced PBMC Proliferation

Dietary lutein did not significantly influence spontaneous proliferation by unstimulated PBMC. There was no significant effect of dietary lutein on PHA-stimulated PBMC response on weeks 0 and 4. However, proliferative response was enhanced (P<0.01) on weeks 8 (10 pg/mL PHA) and 12 (2 and 10 μg/mL PHA) in dogs fed 20 mg lutein compared to unsupplemented dogs. Dogs fed 5 and 10 mg lutein also had higher PBMC proliferation on week 8 in response to 10 μg/ml PHA.

The effects of dietary lutein on Con A-stimulated PBMC proliferative response were generally similar to those observed with PHA-induced proliferation. On weeks 8 and 12, dogs fed 20 mg lutein had higher PBMC proliferation in response to both concentrations of Con A. Dogs fed 10 mg lutein also showed higher PBMC proliferation on weeks 8 and 12 in response to 5 μg/mL Con A. Generally, PBMC proliferation was higher with 5 μg/mL than with 1 μg/mL Con A.

Proliferation of PBMC in response to PWM was generally similar to those observed with PHA and Con A. Dogs fed 20 mg lutein had significantly higher PBMC proliferation on week 8 and 12 in response to both concentrations of PWM as compared to unsupplemented controls. Those fed 10 mg lutein also had higher proliferative response on week 8. Again, no significant treatment difference was observed at weeks 0 and 4.

Natural Killer Cell Cytotoxic Activity

Dietary lutein supplementation did not significantly influence NK cell cytotoxic activity. Specific lysis of target cells by PBMC averaged 49.1±1.1 % across all treatments and sampling periods.

Lyminhocyte Subpopulations

Prior to dietary lutein supplementation (week 0), there were no significant differences in the percentages of any of the lymphocyte markers. On week 12, % CD4+ cells was higher in dogs fed 5 and 10 mg lutein whereas the CD8+ population was not influenced by the diet. On the other hand, dogs fed 20 mg lutein had significantly higher % CD8+ T cytotoxic cells on week 8 compared to control. The ratio of CD4:CD8 was similar among treatments on weeks 0, 4 and 8 but tended to be higher (P<0.08) in dogs fed 10 mg (2.5 0±0.16) compared to control (2.10±0.16).

On weeks 4 and 8, dogs fed lutein generally had higher percentages of CD5+ cells than unsupplemented controls and was statistically significant with dogs fed 5 and 20 mg lutein. Dogs fed 20 mg lutein also had elevated % MHC class 11 cell populations on week 8 and 12 compared to unsupplemented dogs. Dogs fed lower amount of lutein had MHC class 11 populations similar to control.

In contrast to other lymphocyte subpopulations, dietary lutein did not significantly influence the CD21+ B cell population.

Interleukin-2 Production

The production of IL-2 by PHA-stimulated PBMC in whole blood cultures did not differ significantly among dietary treatments throughout the experimental period. Concentrations of IL-2 in culture medium averaged 15.7±0.4 ng/mL throughout the study.

Immunoglobulin Production

Plasma IgG concentrations tended to increase (P>0.05) throughout the 17-week sampling period. Concentrations were similar among dietary treatments during the first 12 weeks of dietary supplementation. However, after revaccination on week 15, plasma IgG was higher (P <0.05) on week 16 in dogs fed 5 mg lutein (P<0.05) and on week 17 in dogs fed 20 mg lutein whereas the concentration of plasma IgM was not changed.

Lipid Peroxidation

Lutein supplementation did not significantly affect plasma TBARS activity which averaged 95.8±0.1 nmol MDA/L across all treatments and periods.

Discussion

The results show that dietary lutein significantly enhances cell-mediated immune response in the dog. Lutein supplementation stimulated the proliferative response of PBMC to PHA, Con A and PWM. There was a marked increase in PBMC proliferation in response to PHA and Con A at week 12 in dogs fed 20 mg lutein.

The data shows that enhanced mitogenesis by dietary lutein is likely attributed to increased population of lymphocytes. Dogs supplemented with lutein had higher populations of CD5+ and CD4+ cells. Dietary lutein may specifically act on T lymphocytes because no changes in B cell population were observed with lutein supplementation.

The data also showed that lutein supplementation significantly increased PWM-induced PBMC proliferation at weeks 8 and 12.

Dietary lutein also significantly increased the DTH response to vaccine, which is indicative of a specific immune response. Lutein supplementation significantly increased the number of cells stained positive for MHC class II molecules compared to unsupplementeci dogs.

Lutein did not significantly affect polyclonal antibody (IgG and IgM) production ex vivo in the canine during the first 12 weeks of supplementation. However, upon reexposure to the antigen, plasma IgG concentrations increased in lutein fed dogs, suggesting an anamnestic effect of dietary lutein in increasing the memory B cells' ability to secrete IgG.

In summary, dietary lutein enhanced canine T-helper cell population and the expression of MHC class II molecules, resulting in increased mitogen-induced canine PBMC proliferation and DTH response. Also, lutein is believed to increase Ig production.

A summary of the results from each of the studies are summarized in Table 1.

TABLE 1

| Benefit | Vitamin E | β-carotene | Lutein |
|---|---|---|---|
| Optimize immune cell activity | ✓ (T-cells) | | ✓ (B-cells) |
| Optimize types of cells present in the blood | | ✓ | |
| Increase antibody levels in the blood | | ✓ | |
| Optimize vaccine recognition by the dog | | ✓ | ✓ |

FIG. 1 illustrates a 20% increase in antibody levels in the blood with the addition of β-carotene to the diet.

Figure 2:
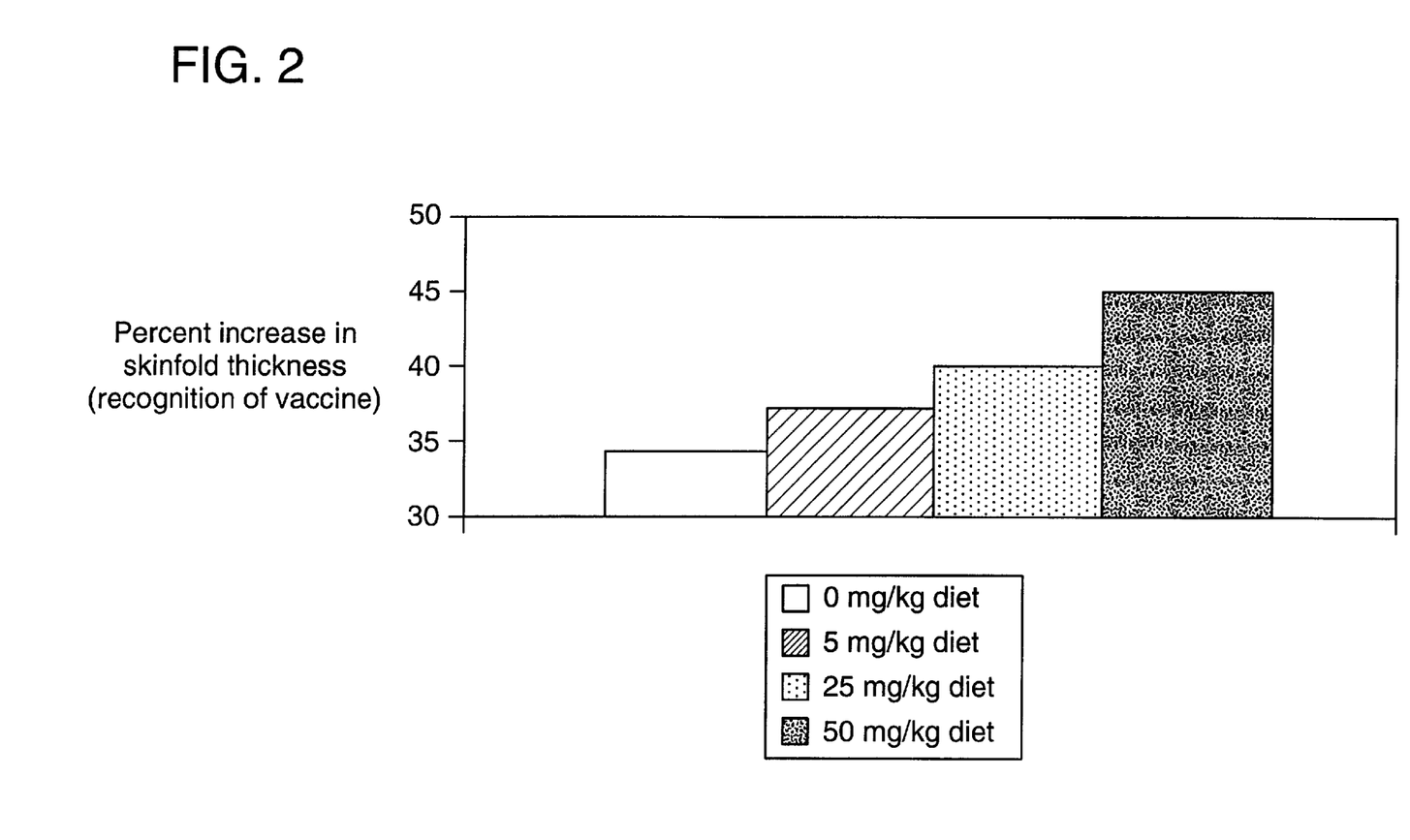
FIG. 2 is a graph illustrating the effect of dietary lutein on vaccine recognition in the dog.

FIG. 2 demonstrates the ability of the dog to recognize a vaccine. As shown, recognition is improved by as much as 32% with the addition of lutein to the diet. This provides the dog with an improved response to vaccinations for additional protection from disease.

It should be noted that no one antioxidant provided benefits to all aspects of the immune system examined. For example, while both vitamin E and lutein optimized immune cell activation, vitamin E worked on the T cells and lutein worked on the B-cells. The improved T-cell function is important for fighting against viral infections and cancer, while the improved B-cell function is important for bacterial infections. Therefore, a combination of antioxidants provides synergistic effects on the immune system that outweigh the benefits of increasing the level of any one antioxidant.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A pet food product for enhancing immune response in a companion animal, said pet food product comprising a pet food composition containing an effective amount of a combination of vitamin E, lutein, and β-carotene, said composition including from about 175 to about 400 IU of vitamin E per kilogram of diet, from about 1 to about 50 mg/day of lutein, and from about 1 to about 50 mg/day of β-carotene.

2. A pet food product for enhancing immune response in a companion animal, said pet food product comprising a pet food composition containing an effective amount of a combination of vitamin E, lutein and β-carotene and further comprising about 18 to 40% crude protein, about 4 to 30% fat, and about 4 to 20% total dietary fiber.

3. A process for enhancing immune response in a companion animal comprising the step of feeding said animal a diet containing an effective amount of a combination of vitamin E, lutein and β-carotene.

4. The process as claimed in claim 1 wherein said diet includes from about 175 to about 400 IU of vitamin E per kilogram of diet, from about 1 to about 50 mg/day of lutein, and from about 1 to about 50 mg/day of β-carotene.

5. The process as claimed in claim 1 wherein said companion animal is a dog.

6. The process as claimed in claim 1 wherein said diet comprises about 18 to 40% crude protein, about 4 to 30% fat, and about 4 to 20% total dietary fiber.

7. A process for optimizing immune cells in a dog comprising the step of feeding said dog a diet containing an effective amount of a combination of vitamin E, lutein and β-carotene.

8. A process for optimizing vaccine recognition in a dog comprising the step of feeding said dog a diet containing an effective amount of a combination of vitamin E, lutein and β-carotene.

* * * * *

UNITED STATES PATENT AND TRADEMARK OFFICE
CERTIFICATE OF CORRECTION

PATENT NO.      : 6,310,090 B1
DATED           : October 30, 2001
INVENTOR(S)     : Michael Griffin Hayek Page 1 of 1

It is certified that error appears in the above-identified patent and that said Letters Patent is hereby corrected as shown below:

Column 12,
Line 43, delete reference to "claim 1" and insert -- claim 3 --, therefor.
Line 47, delete reference to "claim 1" and insert -- claim 3 --, therefor.
Line 49, delete reference to "claim 1" and insert -- claim 3 --, therefor.

Signed and Sealed this

Twenty-fourth Day of December, 2002

JAMES E. ROGAN
*Director of the United States Patent and Trademark Office*

/

(12) INTER PARTES REEXAMINATION CERTIFICATE (814th)
United States Patent
Hayek (10) Number: US 6,310,090 C1
(45) Certificate Issued: Feb. 10, 2014

(54) PROCESS AND PRODUCT FOR ENHANCING IMMUNE RESPONSE IN COMPANION ANIMALS USING A COMBINATION OF ANTIOXIDANTS

(75) Inventor: Michael G. Hayek, Dayton, OH (US)

(73) Assignee: The Iams Company, Dayton, OH (US)

Reexamination Request:
No. 95/001,937, Mar. 13, 2012

Reexamination Certificate for:
Patent No.: 6,310,090
Issued: Oct. 30, 2001
Appl. No.: 09/579,694
Filed: May 26, 2000

Related U.S. Application Data

(60) Provisional application No. 60/136,176, filed on May 27, 1999.

(51) Int. Cl.
*A23K 1/16* (2006.01)
*A23K 1/18* (2006.01)
*A61K 31/352* (2006.01)
*A61K 31/355* (2006.01)

(52) U.S. Cl.
USPC .......................................... 514/458; 514/725

(58) Field of Classification Search
None
See application file for complete search history.

(56) References Cited

To view the complete listing of prior art documents cited during the proceeding for Reexamination Control Number 95/001,937, please refer to the USPTO's public Patent Application Information Retrieval (PAIR) system under the Display References tab.

*Primary Examiner* — Gary Kunz (57) ABSTRACT

A process for feeding a companion animal such as a dog a diet containing an effective amount of a combination of antioxidants to enhance immune response and improve the overall health of the animal is provided. Preferably, the diet includes from about 175 to about 400 IU of vitamin E per kilogram of diet, from about 1 to about 50 mg/day of lutein, and from about 1 to about 50 mg/day of β-carotene.

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1-8 is confirmed.

\* \* \* \* \*